US007846118B2

(12) United States Patent
Sandhu

(10) Patent No.: US 7,846,118 B2
(45) Date of Patent: Dec. 7, 2010

(54) CERVICAL IMMOBILIZATION COLLAR WITH ARTERIAL COOLING ELEMENTS

(75) Inventor: Aqeel A. Sandhu, North Canton, OH (US)

(73) Assignee: Life Core Technologies, LLC, Broadview Heights, OH (US)

( * ) Notice: Subject to any disclaimer, the term of this patent is extended or adjusted under 35 U.S.C. 154(b) by 0 days.

(21) Appl. No.: 12/429,663

(22) Filed: Apr. 24, 2009

(65) Prior Publication Data

US 2009/0209893 A1   Aug. 20, 2009

Related U.S. Application Data

(63) Continuation of application No. 11/162,922, filed on Sep. 28, 2005, now abandoned.

(51) Int. Cl.
*A61F 5/00* (2006.01)
(52) U.S. Cl. .................................. 602/18; 128/DIG. 23
(58) Field of Classification Search ............. 602/17–18; 128/DIG. 23; 607/104, 108
See application file for complete search history.

(56) References Cited

U.S. PATENT DOCUMENTS

| | | | |
|---|---|---|---|
| 4,137,769 A | 2/1979 | Parker | |
| 4,325,254 A | 4/1982 | Svacina et al. | |
| 4,427,010 A | 1/1984 | Marx | |
| 4,745,922 A * | 5/1988 | Taylor | 607/104 |
| 4,783,866 A | 11/1988 | Simmons et al. | |
| 4,832,030 A | 5/1989 | De Canto | |
| 5,005,374 A | 4/1991 | Spitler | |
| 5,007,416 A | 4/1991 | Burns et al. | |
| 5,300,105 A | 4/1994 | Owens | |
| 5,415,624 A | 5/1995 | Williams | |
| 5,575,812 A | 11/1996 | Owens | |
| 5,622,529 A | 4/1997 | Calabrese | |
| 5,626,151 A * | 5/1997 | Linden | 128/897 |
| 5,795,315 A | 8/1998 | Traut et al. | |
| 5,916,242 A | 6/1999 | Schwartz | |
| 6,030,412 A | 2/2000 | Klatz et al. | |
| 6,126,680 A | 10/2000 | Wass | |
| 6,231,535 B1 | 5/2001 | Mainiero et al. | |
| 6,416,532 B1 | 7/2002 | Fallik | |

(Continued)

FOREIGN PATENT DOCUMENTS

WO        00/07529        2/2000

OTHER PUBLICATIONS

International Search Report for corresponding International Application PCT/US05/35095, mailed Jun. 30, 2006.

(Continued)

*Primary Examiner*—Michael A. Brown
(74) *Attorney, Agent, or Firm*—Benesch, Friedlander, Coplan and Aronoff LLP

(57) ABSTRACT

A cervical immobilization collar incorporates one or more cooling elements for inducing a mild cerebral hypothermia by transcutaneous cooling of oxygenated blood flowing through carotid arteries. The immobilization collar includes an annular support structure having an extended axial length for limiting cervical compaction of a wearer's neck and a chin rest for limiting cervical rotation of the wearer's neck. In addition, the one or more cooling elements, which function as a heat extractor, are carried by the support structure in positions for inducing transcutaneous conduction of heat through an anterior portion of the wearer's neck from at least one of the wearer's carotid arteries.

13 Claims, 4 Drawing Sheets

U.S. PATENT DOCUMENTS

| | | |
|---|---|---|
| 6,497,721 B2 | 12/2002 | Ginsburg et al. |
| 6,508,831 B1 | 1/2003 | Kushnir |
| 6,527,798 B2 | 3/2003 | Ginsburg et al. |
| 6,620,188 B1 | 9/2003 | Ginsburg et al. |
| 6,682,552 B2 | 1/2004 | Ramsden et al. |
| 6,865,825 B2 | 3/2005 | Bailey, Sr. et al. |
| 2002/0103520 A1* | 8/2002 | Latham ...................... 607/108 |
| 2003/0055473 A1 | 3/2003 | Ramsden et al. |

OTHER PUBLICATIONS

"Pre-Hospital Cervical Spinal Immobilization of Following Trauma", the Section on Disorders of the Spine and Peripheral Nerves of the American Association of Neurological Surgeons and the Congress of Neurological Surgeons. Sep. 20, 2001.

Office Action issued from United States Patent and Trademark Office in parent U.S. Appl. No. 11/162,922 on Jun. 26, 2008.

Final Office Action issued from United States Patent and Trademark Office in parent U.S. Appl. No. 11/162,922 on Dec. 24, 2008.

* cited by examiner

CERVICAL IMMOBILIZATION COLLAR WITH ARTERIAL COOLING ELEMENTS

CROSS-REFERENCE TO RELATED APPLICATIONS

This application is a continuation of U.S. patent application Ser. No. 11/162,922, filed Sep. 28, 2005.

BACKGROUND OF THE INVENTION

The invention integrates technologies relating to cervical immobilization and to therapeutic induction of mild cerebral hypothermia by transcutaneous cooling of oxygenated blood flowing through carotid arteries.

Brain injuries, such as those produced by blunt trauma or ischemic attack, can produce lasting damage and require long-term treatment or care. Often, brain injuries produced by blunt trauma are suffered by the young, and any resulting disabilities or conditions can be expensive to treat and can require long-term care lasting nearly a lifetime. Brain injuries in general are expensive to treat, but lasting injuries, especially in the young, can impose significant societal burdens.

Brain cooling, i.e., reducing brain temperatures by as little as one or two degrees Celsius, produces a neuroprotective effect against deleterious responses associated with brain injuries. The mild cerebral hypothermia inhibits the release of neuroexcitetory amino acids (e.g., aspartate and glutamine), thereby interrupting the cascading effects of the inflammatory response. The neuroprotective effect is most pronounced if brain cooling is effected as soon as possible following an injury.

One way of cooling the brain is by withdrawing heat from the blood supply to the brain. For example, a mild cerebral hypothermia can be induced by transcutaneous conduction of heat from one or both of the carotid arteries accessible through the carotid triangles of the neck. Endothermic heat extractors positioned over the carotid triangles can be used to cool blood flowing into the brain.

Although the neuroprotective effects of even mild cerebral hypothermia have been well documented, along with the importance of initiating such cooling as soon as possible following a brain injury, protocols for first responders generally do not incorporate effective procedures for initiating brain cooling. For example, blunt head trauma is often associated with the risk of cervical injury, and the routine application of conventional cervical immobilization collars can block effective cooling of neck tissue close to the carotid arteries. Even if early brain cooling is a treatment option for cases of obvious blunt head trauma, other brain injuries can be difficult to detect on site, especially if there are few outward signs or the inflammatory response is slow to develop.

SUMMARY OF INVENTION

The invention among its preferred embodiments includes new procedures for first responders to mitigate brain injuries and new apparatus for inducing brain cooling within cervical immobilization collars used to stabilize patients for transport. Patients at risk of almost any sort of injury are routinely fitted with cervical immobilization collars for transport, and the invention incorporates heat extractors within the immobilization collars in positions for conducting heat from one or preferably both carotid arteries. With the modified immobilization collars, first responders can induce a mild cerebral hypothermia in patients both with and without obvious signs of brain insults or injuries. Those without any sort of brain insult or injury suffer no ill consequences, but those with brain insults or injuries enjoy neuroprotective effects that lessen the chances for lasting brain damage.

One version of the invention as a cervical immobilization collar includes an annular support structure having an extended axial length for limiting cervical compaction of a wearer's neck and a chin rest for limiting cervical rotation of the wearer's neck. A heat extractor carried by the support structure is positioned for inducing a transcutaneous conduction of heat through an anterior portion of the wearer's neck from at least one of the wearer's carotid arteries.

The heat extractor, which can take the form of one or more endothermic packs, can be carried by the support structure in a position for directly contacting the anterior portion of the wearer's neck. Alternatively, a thermally conductive material can be arranged for contacting the anterior portion of the wearer's neck for conducting heat from the wearer's neck to the heat extractor. The thermally conductive material can be compliant to conform to the wearer's neck and thereby increase an area of contact with the anterior portion of the wearer's neck. For example, the thermally conductive material can be polymer foam. The annular support structure itself or an anterior portion thereof can also be made of a thermally conductive material. The endothermic packs can be mounted exterior to the annular support structure but in thermal contact with the thermally conductive material, which is itself in contact with the anterior portion of the wearer's neck.

The heat extractor can be made as an activatable heat extractor that is connected to the support structure so that certain movements of the support structure automatically activate the heat extractor for extracting heat. For example, the heat extractor can be activated by movements associated with the installation of the support structure around the wearer's neck. The annular support structure can have a first form for storage and a second form for use installed around the wearer's neck. Conventional heat extractors, such as endothermic packs activated by distortion, can be mounted so that the change in the support structure shape from the first form to the second form imparts the required distortion for activating the endothermic packs. The support structure can also be stored in an anatomic form close to the form of its intended use but can be temporarily deformed for mounting the support structure on a wearer's neck or can be subject to an adjustment or securing operation, any one of which can be exploited for activating the endothermic packs.

An opening formed through the annular support structure can be aligned with the wearer's carotid triangle for allowing the wearer's pulse to be taken with the support structure installed around the wearer's neck. The heat extractor can be temporarily displaced in the vicinity of the opening in the support structure to allow access to the wearer's carotid triangle for taking the wearer's pulse.

A sensor arrangement can also be carried by the support structure proximate to the wearer's neck for monitoring one or more circulatory parameters. The sensor arrangement preferably monitors at least one of arterial oxygen saturation, heart rate, blood pressure, and blood temperature. One or more displays can be mounted on the support structure for displaying the measured circulatory parameters. Recording devices and communication ports for transferring data from the sensors to an external device can also be mounted on the support structure. Other sensors can be arranged for monitoring neck temperature within the carotid triangle or temperature differentials between different portions of the neck. In addition, sensors, including thermochromic indicators, can be arranged for monitoring the temperature of the heat extractors for assessing their performance and for determining if the heat extractors require replacement.

Another version of the invention as a protocol for treating trauma patients includes installing a cervical immobilization collar around a patient's neck having facility for limiting rotation and compaction of the patient's cervical vertebrae. At least one activatable cooling element carried by the collar is arranged in thermal transcutaneous communication with at least one of the patient's carotid arteries through an anterior portion of the patient's neck. The at least one activatable cooling element is activated in association with the installation of the collar, thereby initiating a flow of heat from the one or more carotid arteries through the anterior portion of the patient's neck to the cooling element for reducing the temperature of the patient's brain without inducing systemic hypothermia.

The activatable cooling elements can be placed in direct or indirect thermal contact with the anterior portion of the patient's neck and can be of a type activated by distortion. Preferably, the cooling elements are activated automatically through manipulations of the collar associated with its installation. For example, the cooling elements can be arranged for activation by changing a shape of the collar from a first form for storage to a second form for use around the patient's neck. Alternatively, the collar can be stored in an anatomic form close to the form of its intended use, but the cooling elements can still be automatically activated by temporarily deforming or otherwise subjecting the collar to adjustment or securing operations for mounting the collar around the patient's neck.

Parameters related to both the circulatory performance of the patient and the thermal performance of the heat extractor can be monitored. Such parameters as arterial oxygen saturation, pulse rate, blood pressure, and blood temperature can be monitored by appropriate sensors mounted in the collar. In addition, the temperature of the heat extractor can be monitored to assess its performance or need for replacement. Alternatively, circulatory measurements, such as pulse rate, can be taken manually or independently by temporarily displacing the cooling element through an opening in the collar.

Another version of the invention as a modular cervical immobilization collar also includes an annular support structure having an extended axial length for limiting cervical compaction of a wearer's neck and a chin rest for limiting cervical rotation of the wearer's neck and a cooling element for extracting heat from a carotid artery of the wearer's neck. A release surface of the support structure cooperates with the cooling element to form a temporary bond for removably mounting the cooling element on the support structure.

Preferably, the cooling element includes an adhesive layer that is arranged to temporarily bond to the release surface of the support structure. The adhesive layer of the cooling element can be temporarily bonded to a release liner until the cooling element is readied for bonding to the release surface of the support structure.

Another modular cervical immobilization collar arranged in accordance with the invention includes, in addition to the above-referenced annular support structure, both a cooling element for extracting heat from a carotid artery of the wearer's neck and a pad for conforming to the wearer's neck. Both the cooling element and the pad are arranged for mounting from the inside surface of the support structure in contact with the front of the wearer's neck. A mounting system of the support structure alternatively mounts the cooling element or the pad in contact with the front of the wearer's neck.

With the pad mounted on the inside surface of the support structure, the collar functions as a conventional cervical immobilization collar for stabilizing a wearer's cervical vertebrae. However, if brain injury is suspected, the pad can be removed and replaced by the cooling element for inducing a mild cerebral hypothermia while still providing similar cervical stabilization. The cooling element preferably includes reactants for an exothermic reaction and has a ribbed form to limit redistribution of the reactants.

Yet another version of the invention as a cervical immobilization collar includes the above-referenced annular support structure having an extended axial length for limiting cervical compaction of a wearer's neck and a chin rest for limiting cervical rotation of the wearer's neck in which at least a portion of the annular support structure is thermally conductive. A cooling element is mounted in thermal communication with the thermally conductive portion of the support structure for extracting heat from a carotid artery in the wearer's neck.

The support structure includes an inside surface proximate to the wearer's neck and an outside surface remote from the wearer's neck, and the cooling element can be mounted on the outside surface of the support structure. A thermally conductive pad can be mounted on an inside surface of the support structure for thermally communicating an anterior portion of the wearer's neck. The cooling element preferably extracts heat from the wearer's carotid artery by transfers of heat through both the thermally conductive pad and the thermally conductive portion of the support structure.

BRIEF DESCRIPTION OF THE DRAWING FIGURES

DETAILED DESCRIPTION

Figure 1:
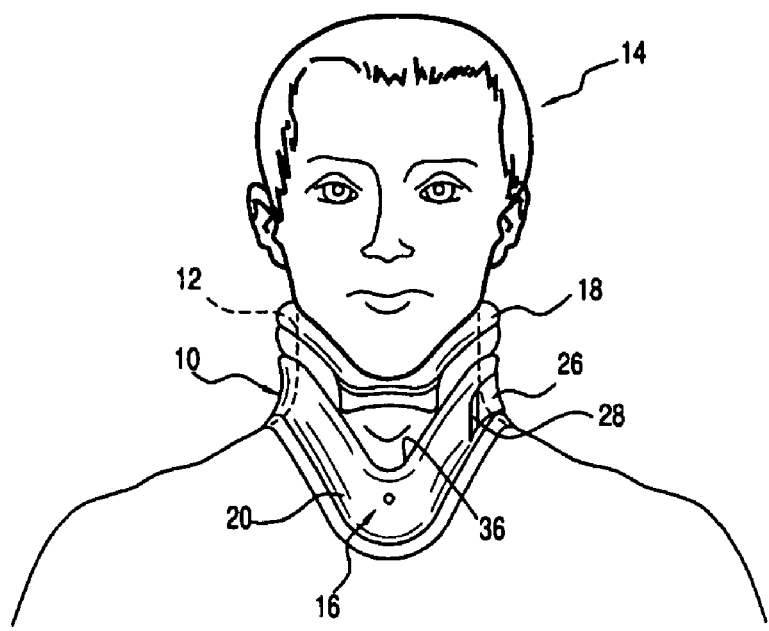
FIG. 1 is a front view of a cervical spine immobilization collar in accordance with the invention mounted around a wearer's neck.

A cervical immobilization collar 10 in accordance with the invention is shown in FIG. 1 mounted in place about the neck 12 of a patient or other wearer 14 for purposes of both cervical spine immobilization and transcutaneous cooling of blood flowing through the wearer's carotid arteries. A support structure of the collar 10 includes a main body 16 having an extended axial length that limits cervical compaction of the wearer's neck 12 and a chin rest 18 for limiting cervical rotation of the wearer's neck 12.

Figure 2:
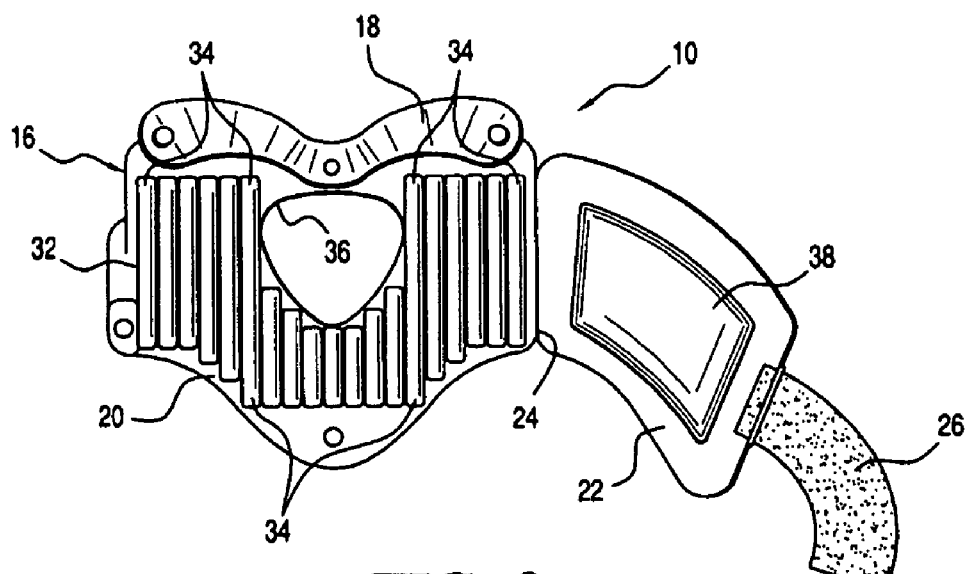
FIG. 2 is a rear view of the cervical spine immobilization collar showing endothermic packs mounted inside the collar.

Referring also to FIG. 2, the main body 16 includes an anterior portion 20 and a posterior portion 22. One end of the anterior portion 20 is connected to one end of the posterior portion 22 by an integral joint 24 or other preferably permanent connection. The main body can be formed (preferably by molding) from a variety of materials including plastics, polymers, or carbon or poly-paraphenylene terephthalamide fiber. A hook and loop fastener strap 26 extends from the other end of the posterior portion 22 for temporarily engaging a mating hook-and-loop fastener patch 28 mounted on the other end of the anterior portion 20 of the main body 16. FIG. 1 shows the hook and loop fastener strap 26 engaged with its mating fastener patch 28 for closing the collar 10 around the wearer's neck 12. FIG. 2 shows the hook-and loop fastener strap 26 disengaged from its mating fastener patch 28 for opening the collar 10.

Lining an inside surface 32 of the anterior portion 20 of the main body 16 is a ribbed cooling element 34 (i.e., heat extractor) in the shape of tubes. The cooling element 34 can be temporarily or permanently mounted. For example, the cooling element 34 can be held in place by a pressure-sensitive adhesive. Fugitive adhesives or release coatings can be used to make less permanent bonds. Although depicted as an array of tubes, the cooling element 34 can take a variety of forms, including being shaped as a single packet. The tubes, themselves, are preferably at least partly connected to each other with a common web, so the cooling element 34 can be mounted on the support structure in one piece. A foam pad 38 lines the posterior portion 22 of the main body 16 to provide a better fit with the posterior portion of the wearer's neck.

When the collar 10 is mounted in place on the wearer's neck 12, the cooling element 34 directly overlies the carotid triangles of the wearer's neck 12 and functions as a heat extractor for withdrawing heat from blood flowing through the wearer's carotid arteries. Preferably, the cooling element 34 conforms to the particularities of individual wearer's necks 12, thereby maximizing skin contact area for more efficiently withdrawing heat from neck tissues adjacent to the carotid arteries. The ribbed structure of the cooling element 34 preferably maintains more even fluid distributions throughout the cooling element 34. An opening 36 within the anterior portion 20 of the collar 10 provides clearance for movement of the wearer's Adams apple.

Endothermic reactions, previously chilled gels, or other materials having the capacity to absorb significant amounts of heat can effect the heat extraction function of the cooling element 34. Preferably, the cooling element 34 includes one or more endothermic packs, such as those containing compartments of ammonium nitrate and water separated by rupturable membranes. Deforming the cooling elements 34 so as to apply differential pressure between the compartments or to otherwise break the membrane can activate such cooling elements 34. Once the components of the endothermic packs are mixed or otherwise activated, the collar 10 is preferably put into immediate use.

Figure 3:
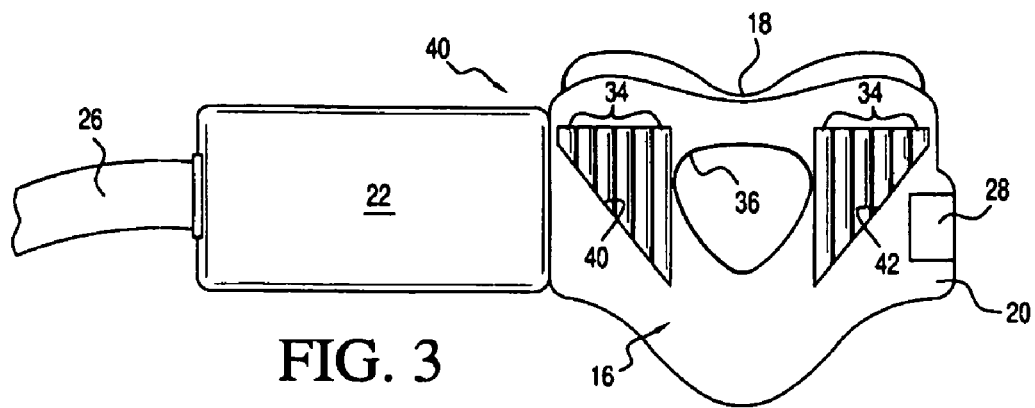
FIG. 3 is a front view of an alternative cervical immobilization collar containing apertures for physically accessing the carotid arteries.

The front view of FIG. 3 shows an alternative cervical immobilization collar 40 having many features in common with the cervical mobilization collar 40. However, the anterior portion 20 of the support structure is modified by the addition of two apertures 40 and 42 that provide physical access to the carotid triangles of the wearer's neck 12. The cooling element 34 can be temporarily separated or otherwise displaced through either of the apertures 40 and 42 to allow access to the wearer's carotid triangle for taking the wearer's pulse. The cooling element 34 within the aperture 42 is shown temporarily displaced in FIG. 3.

Figure 4:
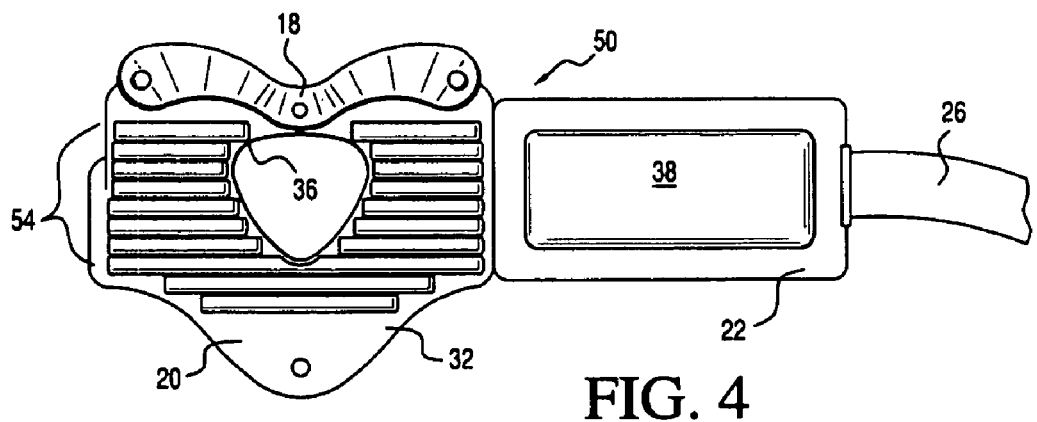
FIG. 4 is a rear view of an alternative cervical immobilization collar with endothermic packs oriented horizontally for activation when the collar is bent during installation.

The rear view of FIG. 4 shows an alternative cervical immobilization collar 50 with a different orientation of a ribbed cooling element 54, still substantially in the form of tubes but oriented horizontally instead of vertically. The cooling element 54 is preferably attached to the anterior portion 20 of the support structure by an adhesive or other fastening means while the support structure is stored in a substantially flat state. When the anterior portion 20 in combination with the posterior portion 22 is curled for use around the wearer's neck 12, the horizontally oriented cooling element 54 bends with the anterior portion 20 into partially curled shape that reduces the volume of individual tubes within the cooling element 54. The reduced volume produces a pressure differential within the cooling element 54 that triggers an endothermic reaction. For example, the differential pressure can rupture one or more membranes separating two endothermic reactants.

Alternatively, the collar 50 can be stored in a more anatomical form closer to the form of its intended use. As such, the cooling element 54 remains in a deactivated state while the anterior portion 20 is maintained in a predetermined curled shape. However, the anatomically curled collar 10 can be temporarily deformed to fit around a wearer's neck, and stress associated with the temporary deformation can be used to rupture one or more membranes separating endothermic reactants within the cooling element 54. For example, the membranes can be made from a frangible material that can be broken by stress associated with a change in shape.

Any of the collars 10, 40, or 50, can be stored in a condition (flat or curled) without their cooling elements 24, 34, or 54, which can be later mounted in place when the collars 10, 40, or 50 are put into use. The act of mounting the cooling elements 24, 34, or 54, as well as deliberate manipulations of the cooling elements 24, 34, or 54, themselves, can be used to activate the cooling elements 24, 34, or 54.

Figure 5:
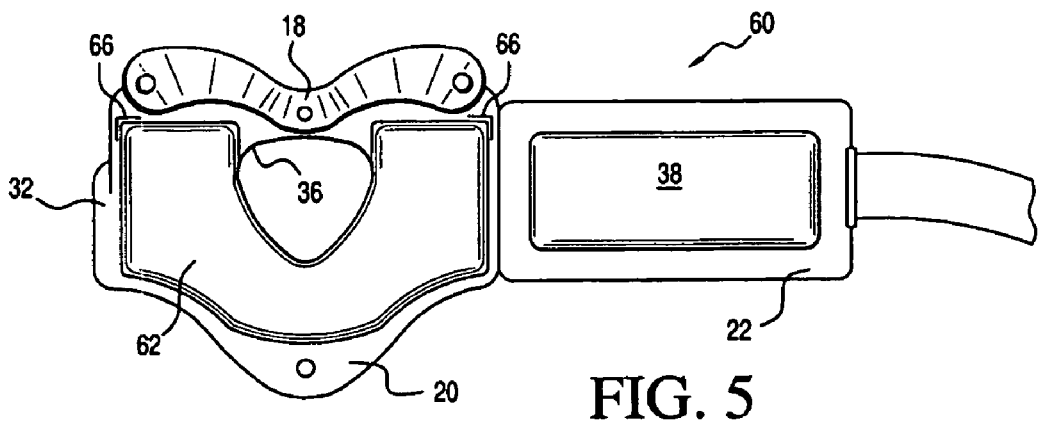
FIG. 5 is a rear view of another alternative cervical immobilization collar incorporating thermally conductive foam that conforms to the anterior portion of the wearer's neck and conducts heat to cooling elements mounted elsewhere on the collar.

A cervical immobilization collar in accordance with the invention can also be fashioned as an alternative use collar. For example, cervical immobilization collar 60, as shown in FIG. 5, can be fitted with a removable neck-conforming foam pad 62 intended for use is situations without risk of brain injury. The removable foam pad 62, which can be attached to the support structure by a removable adhesive or other temporary mounting structure, occupies substantially the same space as the cooling elements 24, 34, or 44. However, for situations where brain injury is suspected, the removable foam pad 62 can be removed and replaced by a similarly shaped pattern of cooling elements 24, 34, or 44. Alignment marks 66 or other guide structures can be used to assist in the proper placement of the removable foam pad 62 or the cooling elements 24, 34, or 44 as situations dictate.

Figure 6:
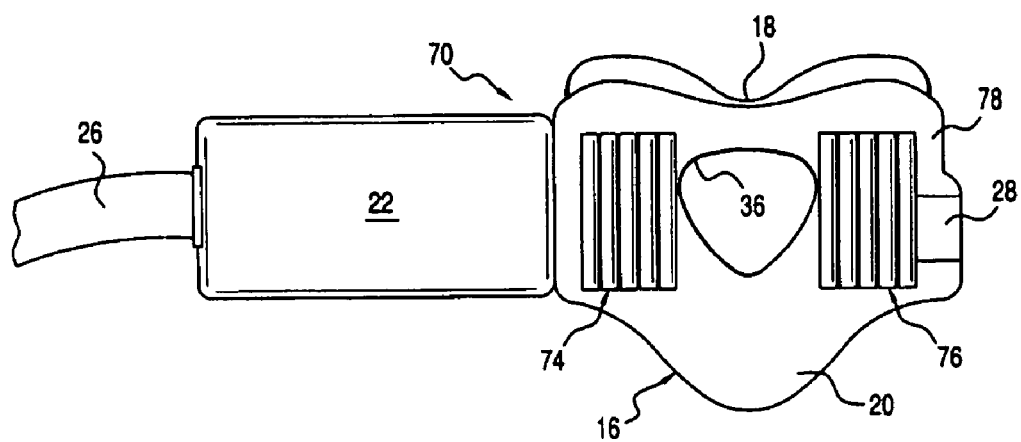
FIG. 6 is a front view of another alternative cervical immobilization collar with cooling elements mounted form an outside surface of a conductive support structure.

In FIG. 6, a cervical immobilization collar 70 is shown with cooling elements 74 and 76 mounted on an outside surface 78 of the support structure. The cooling elements 74 and 76 thermally communicate with the intended wearer's neck by a thermally conductive pathway through the collar 70. For example, the anterior portion 20 of the main body 16 can be made of a conductive material, such as a thermally conductive polymer, for conducting heat from the anterior portion of the wearer's neck. In addition, a foam structure, such as the foam pad 62 depicted in the proceeding embodiment, can also be made of a conductive material to more efficiently conduct heat from the appropriate areas of the wearer's neck. The thermally conductive foam pad more intimately contacts the wearer's neck to provide a more efficient thermal pathway to the cooling elements 74 and 76.

The thermally conductive materials can be formed from a variety of base resins including polypropylene, acrylonitrile butadiene styrene, polybutyleneterephthalate, polyamide, polycarbonate, polyphenylene sulfide, liquid crystal polymers, and polyetheretherketone. Additives, such as discontinuous graphite fibers, can be added to promote thermal conductivity. Thermally conductive plastics can also be made electrically insulative, as is preferred, for protecting wearers against electric shock.

Absent the cooling elements 74 and 76, the cervical immobilization collar 70 with conductive portions (e.g. the anterior portion 20 and the foam pad 62) is fully functional for stabilizing patients. However, if brain injury is suspected, the cooling element 74 can be attached to the outside surface 78 of the anterior portion 20 as shown in FIG. 6 for extracting heat from the patient's carotid arteries.

Figure 7:
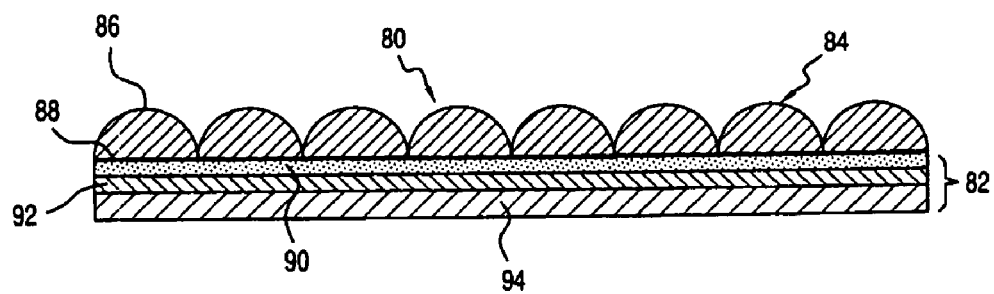
FIG. 7 is a cross-section view of a cooling element structure mounted on a release liner prior to installation on a cervical immobilization collar.

FIG. 7 shows a modular cooling element structure 80 temporarily mounted on a release liner 82. Cooling element 84 has a similar ribbed structure between top and bottom webs 86 and 88. A layer 90 of pressure sensitive adhesive is applied to a bottom surface of the bottom web 88. The release liner 82 includes a substrate 94, such as paper, covered by a layer 92 of release, such as silicone. The release liner 82 protects the layer 90 of pressure sensitive adhesive until the cooling element 84 is needed for use. In addition, the release liner 82 is removable for exposing the pressure-sensitive adhesive layer 90 on the bottom web 88 of the cooling element 84. The adhesive layer 90 can be used to bond the cooling element to an inside or outside surface 32 or 78 of one of the immobilization collars 10, 40, 50, 60, or 70. Preferably, the inside or outside surface 32 or 78 of the immobilization collar 10, 40, 50, 60, or 70 intended for mounting the cooling element 84 is coated with a release or is otherwise formed as a release surface to allow the cooling element 84 to be repositioned, removed, or replaced as needed. The adhesive of the adhesive layer 90 can be a thermally conductive adhesive, especially for bonding to a thermally conductive support structure.

Separate cooling elements (as shown in FIG. 6) can be provided for each of a wearer's two carotid arteries so that each of the cooling elements is removable and replaceable one at a time for such purposes as providing temporary access to either of the patient's carotid arteries. More flexibility is possible in the placement of cooling elements when the cooling elements are mounted on conductive structures that are in thermal communication with the carotid triangles of the wearer's neck. Even if the cooling elements are mounted on an inside surface of the immobilization collar, benefits can still be obtained by forming at least the anterior portion of the collar from a thermally conductive material or embedding the cooling elements within a thermally conductive foam. The addition of thermally conductive support structures can provide an enlarged heat sink interconnecting individual cooling elements and can provide for mounting cooling elements on both the inside and outside surfaces 32 and 78 of the immobilization collar to speed the extraction of heat.

Figure 8:
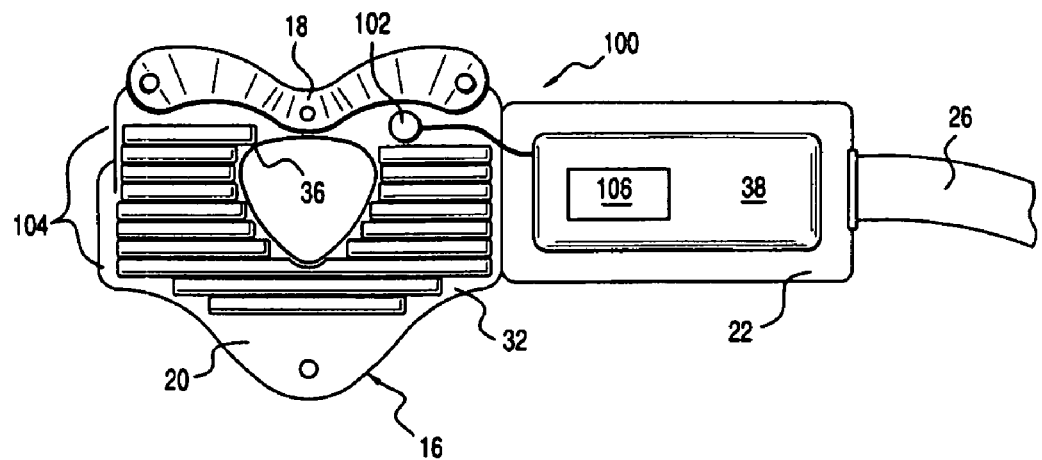
FIG. 8 is a rear view of yet another alternative cervical immobilization collar showing a sensor mounted on an inside surface for monitoring one or more circulatory parameters.

FIG. 8 shows a similar cervical immobilization collar 100 incorporating a sensor 102 mounted in the vicinity of one of the wearer's carotid triangle for monitoring one or more circulatory parameters such as arterial oxygen saturation, heart rate, blood pressure, and blood temperature. For positioning the sensor 102 in direct contact with the patient's skin, a portion of the cooling element 104 may need to be reshaped or displaced. A recording device 106 can be located elsewhere inside or outside the collar for recording information collected by the sensors. Other sensors can be mounted elsewhere in the collar 100 for monitoring various body parameters, including body temperature, or for monitoring performance of the immobilization collar itself. For example, a temperature gauge 110, such as a thermochromic strip, can be used for monitoring the temperature of the collar 100 or the cooling element 104.

Figure 9:
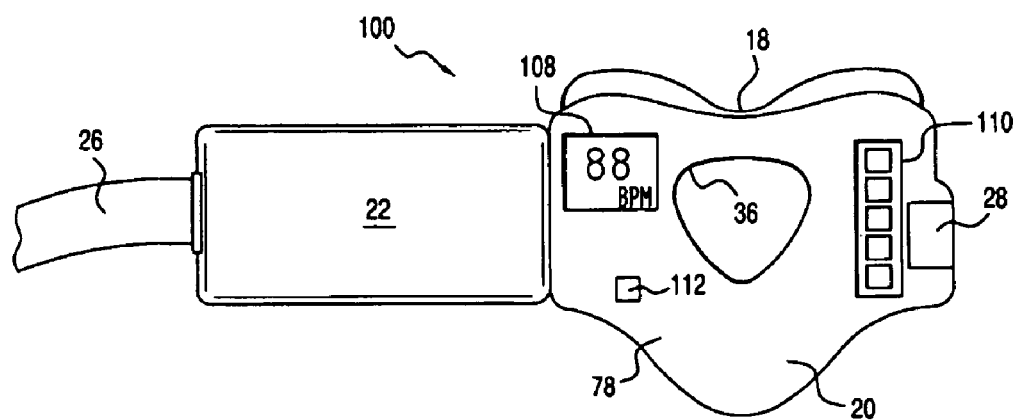
FIG. 9 is a front view of the cervical immobilization collar of FIG. 8 showing a display device for displaying data from the circulatory data sensor as well as a communication port and a temperature gauge for monitoring performance of the cooling element.

A display 108 is shown in FIG. 9 visible on the outside surface 78 of the anterior portion 20 of the same cervical immobilization collar 100. The display 108 can be used for monitoring the circulatory data collected by the sensor 102 as well as other data collected by other sensors mounted in the collar 100. A communications port 112 can also be formed in the collar for transferring data from the one or more sensors to an external device.

The cervical immobilization collars 10, 40, 50, 60, 70, and 100 make possible a new protocol for treating trauma patients, including patients at risk for head trauma or ischemic attack. The treatment centers on installing a cervical immobilization collar around a patient's neck having facility for limiting rotation and compaction of the patient's cervical vertebrae. At least one activatable cooling element is carried by the collar in a position for thermal transcutaneous communication with at least one of the patient's carotid arteries through an anterior portion of the patient's neck. The cooling element is activated in association with the installation of the collar around the patient's neck for initiating a flow of heat from the one or more carotid arteries through the anterior portion of the patient's neck to the cooling element for reducing temperature of the patient's brain without inducing systemic hypothermia.

If the cooling element is located on an inside surface of the cervical immobilization collar, the cooling element is preferably mounted in place before the collar is installed on a patient. However, if the cooling element is located on an outside surface of the cervical immobilization collar, the cooling element can be mounted on the collar either before or after the collar is installed on a patient. A modular collar, incorporating the option of mounting a cooling element or a foam pad on an inside surface of the collar, can require the removal and replacement of a foam pad with the cooling element. If mounted just prior to use, the cooling element can be activated just before or during their mounting on the collar.

Alternatively, the cooling element can be pre-positioned in place on the cervical immobilization collar and can be automatically activated by the usual or slightly exaggerated manipulations of the collar used for installing the cervical immobilization collar on a patient. Distortions of the cooling element caused by the manipulations of the collar can be used to activate the cooling element. For example, the cooling element can be activated by changing a shape of the collar from a first form for storage to a second form for use around the patient's neck. Subjecting the collar to adjustment or securing operations for mounting the collar around the patient's neck can also activate the cooling element.

The new protocol can also include monitoring one or more parameters related to circulatory performance of the patient through one or more sensors carried by the cervical immobilization collar. The monitored parameters can include oxygen saturation, pulse rate, blood pressure, or blood temperature. Sensors can also be used to monitor the thermal performance of the cooling element. The protocol of claim can also include measuring a pulse rate of the patient manually by temporarily displacing the cooling element from an opening in the collar over the patient's carotid triangle.

Although the invention has been described with respect to a limited number of embodiments, many more variations will be readily apparent to those of skill in the art in accordance with the overall teaching and scope of this invention. For example, the cooling elements could be mounted on both the anterior and posterior portions of the cervical immobilization collar to extract heat from larger portions of the wearers' necks. The cooling of both carotid arteries is generally preferred, but the cooling elements could also be fashioned for cooling just one of the carotid arteries, leaving the other carotid artery exposed for other purposes.

The invention claimed is:

1. A cervical immobilization collar comprising an annular support structure having an extended axial length for limiting cervical compaction of a wearer's neck and a chin rest for limiting cervical rotation of the wearer's neck,
a heat extractor carried by the support structure comprising at least one rupturable membrane,
the heat extractor being located within the annular support structure so that when the annular support structure is positioned about the wearer's neck for limiting cervical compaction and cervical rotation of the wearer's neck, the heat extractor is positioned in thermal contact with an anterior portion of the wearer's neck, and
the heat extractor being connected to the annular support structure so that changing the position of the support structure from a first position to a second position, in association with the installation of the support structure around the wearer's neck, automatically activates the heat extractor by breaking the rupturable membrane in the heat extractor, producing an endothermic reaction within the heat extractor.

2. The immobilization collar of claim 1, wherein the heat extractor comprises an endothermic pack activated by breaking the at least one rupturable membrane.

3. The immobilization collar of claim 1, wherein the annular support structure is stored in a first position, the first position being an anatomic form close to a form of its intended use and is temporarily distortable into the second position for mounting the support structure on a wearer's neck, wherein a change in the support structure shape associated with the temporary distortion of the support structure from the first position to the second position breaks the at least one rupturable membrane, producing the endothermic reaction.

4. The immobilization collar of claim 1, wherein the annular support structure is subject to an adjustment or securing operation, wherein a change in the support structure shape from the first position to the second position is associated with the adjustment or securing operation and breaks the rupturable membrane, producing the endothermic reaction.

5. The immobilization collar of claim 1, further comprising a sensor arrangement carried by the support structure proximate to the wearers neck for monitoring one or more circulatory parameters, and the sensor arrangement being arranged to monitor at least one of arterial oxygen saturation, heart rate, blood pressure, and blood temperature.

6. The immobilization collar of claim 5, further comprising one or more displays mounted on the support structure for displaying data related to the measured circulatory parameters.

7. The immobilization collar of claim 5, further comprising at east one recording device mounted on the support structure for recording data related to the measured circulatory parameters.

8. The immobilization collar of claim 5, further comprising a communication port mounted on the support structure for transferring data from the one or more sensors to an external device.

9. A protocol for treating trauma patients, comprising:
providing a cervical immobilization collar comprising at least one activatable cooling element comprising at least one rupturable membrane, the activatable cooling element located within the cervical immobilization collar so that when the cervical immobilization collar is positioned about the wearer's neck, the activatable cooling element is positioned in thermal contact with an anterior portion of the wearer's neck,
installing the cervical immobilization collar around a patient's neck by changing the shape the cervical immobilization collar from a first position, associated with the storage of the cervical immobilization collar, to a second position associated with the installation of the cervical immobilization collar around the wearer's neck,
wherein the at least one cooling element is automatically activated when the at least one rupturable membrane is broken by moving the cervical immobilization collar from the first position to the second position.

10. The protocol of claim 9, wherein installing the cervical immobilization collar involves temporarily distorting or otherwise subjecting the cervical immobilization collar to adjustment or securing operations for mounting the collar around the patient's neck.

11. The protocol of claim 9, wherein the first position is an anatomically curved shape for fitting the collar around the patient's neck.

12. The protocol of claim 9, wherein the first position comprises having the cooling element is pre positioned on an inside surface of the cervical immobilization collar and storing the cervical immobilization collar in the first position prior the installation of the collar around the patient's neck.

13. The protocol of claim 12, wherein the cooling element is removably attached to the inside surface of the cervical immobilization collar.

* * * * *